United States Patent [19]
Will

[11] Patent Number: 6,134,475
[45] Date of Patent: Oct. 17, 2000

[54] THERAPEUTIC DEVICE

[76] Inventor: Frank J. Will, 18222 NW. 15th Ct., Pembroke Pines, Fla. 33029

[21] Appl. No.: 09/012,176

[22] Filed: Jan. 22, 1998

Related U.S. Application Data

[60] Provisional application No. 60/037,641, Jan. 22, 1997.
[51] Int. Cl.⁷ ...................................................... A61F 7/00
[52] U.S. Cl. .................................. 607/98; 607/99; 606/9
[58] Field of Search ................................... 606/9, 27, 28; 607/96, 98, 99, 100, 101, 108, 109; 219/527, 528, 529

[56] References Cited

U.S. PATENT DOCUMENTS 5,991,666  11/1999  Vought ........................................ 607/98

*Primary Examiner*—Linda C. M. Dvorak
*Assistant Examiner*—R. Kearney
*Attorney, Agent, or Firm*—Plunkett & Cooney, P.C.

[57] ABSTRACT

A therapeutic device utilizes a flexible circuit board for generating heat in localized dermal areas. A source of power such as a battery is operably connected to the flexible circuit board. A pulse width modulator is interposed the source of energy and the circuit board to control the amount of heat generated thereby. The therapeutic device may be used conjointly with an adhesive bandage strip or gauze pad to absorb any body fluids secreted by the user in response to the heat generated by the device such as by a dermal eruption or the like.

3 Claims, 2 Drawing Sheets

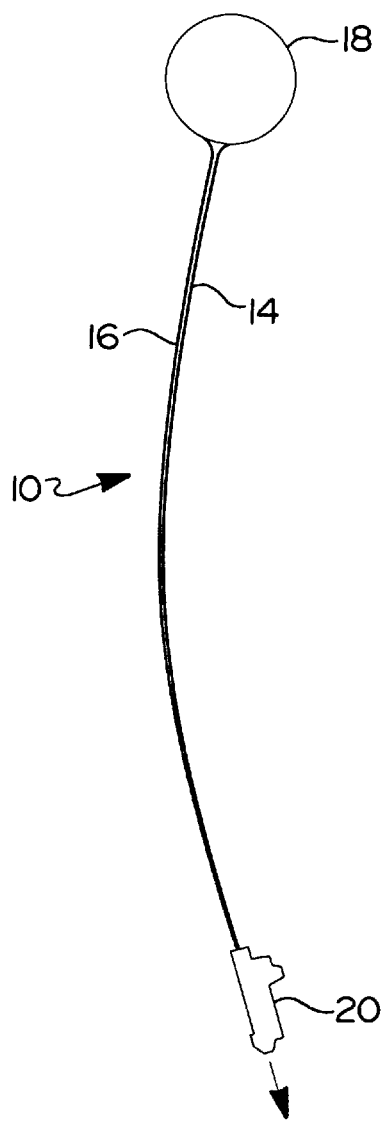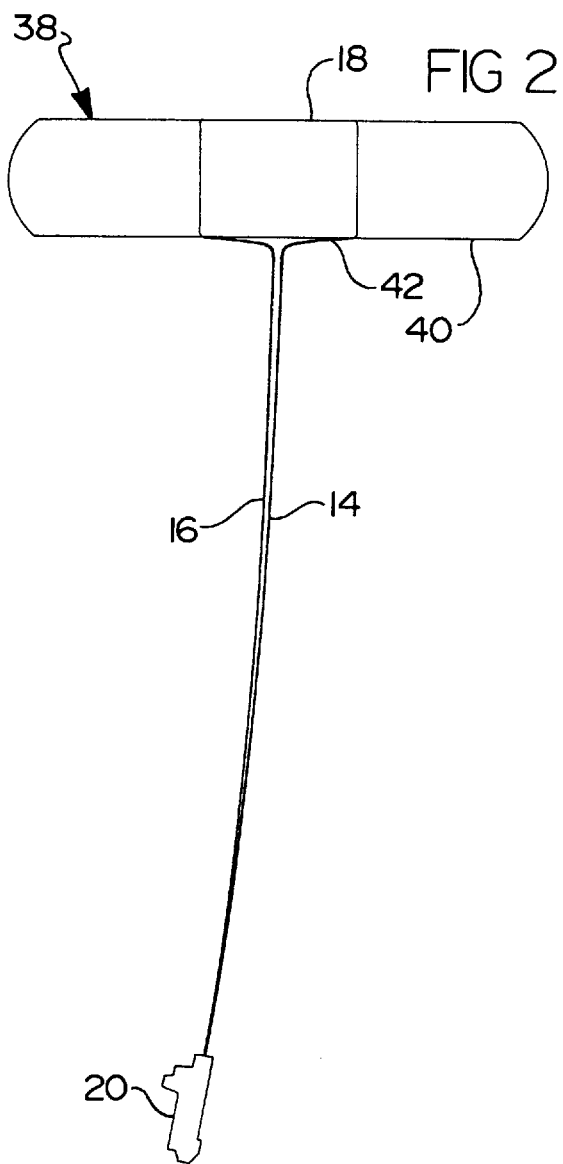

THERAPEUTIC DEVICE

CROSS REFERENCE TO RELATED APPLICATIONS

This application claims the benefit under 35 U.S.C. 119(e) U.S. provisional patent application Serial No. 60/037,641, filed Jan. 22, 1997.

STATEMENT REGARDING FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention pertains to therapeutic devices. More particularly, the present invention pertains to therapeutic devices for topically applying heat. Even more particularly, the present invention pertains to therapeutic devices for topically applying heat to localized areas of a user's body.

2. Prior Art

At the outset, it is to be noted, and as is known to those of ordinary skill in the art to which the present invention pertains, skin or dermal eruptions such as sebaceous cysts, boils, pimples and similar skin conditions are not only unattractive in appearance but create a great deal of discomfiture. Ordinarily, the pain and pressure caused by these dermal eruptions are relieved by causing them to come to a "head". Usually, thereafter the head is lanced or otherwise broken to draw the pus therefrom. Bringing these eruptions to a head is usually accomplished through ointments, by time lapse or through other skin treatments. During that period of time while waiting for the eruption to come to a head causes the discomfiture heretofore described. As will be detailed hereinbelow, and as will be appreciated by one of ordinary skill in the art to which the present invention pertains the present invention, in a particular application thereof, accelerates the head formation on such dermal eruptions. Moreover, and in a further aspect of the present invention, and as will be appreciated, the present invention provides a quick and convenient way of applying heat to a localized area where topical application of heat is desired.

The prior art has taught heating devices for local topical use of various sizes and shapes. See, for example, inter alia, U.S. Pat. Nos. 3,108,596; 4,303,074; 4,335,725; 4,585,002; 4,607,624; 4,736,088, and; 5,545,190. However, it is to be appreciated that none of these devices are enabled—as being cooperable with gauze padding or the like to provide localized heating and body fluid absorption capabilities.

SUMMARY OF THE INVENTION

The present invention generally provides for a therapeutic device for imparting localized heat to portions of the body of a user. The device hereof, generally, comprises:

(a) a source of electrical energy;

(b) means for conducting electrical energy from the source; and (c) a resistive element comprising a flexible circuit board in electrical communication with the means for conducting electricity.

The resistive element cooperates with a pulse width modulator to vary the intensity and duration of the heat generated by the resistive element.

In a further embodiment hereof the therapeutic device is integrated into and cooperates with a gauze pad provided a localized heat generating bandage.

For a more complete understanding of the present invention references made to the following detail description and accompanying drawing. In the drawing, like reference characters refer to like parts throughout the several views in which:

BRIEF DESCRIPTION OF THE DRAWING

FIG. 1 is a plan view of a therapeutic device in accordance with the present invention;

FIG. 2 is a plan view of the therapeutic device hereof in combination with a bandage;

DESCRIPTION OF THE PREFERRED EMBODIMENT

Figure 3:
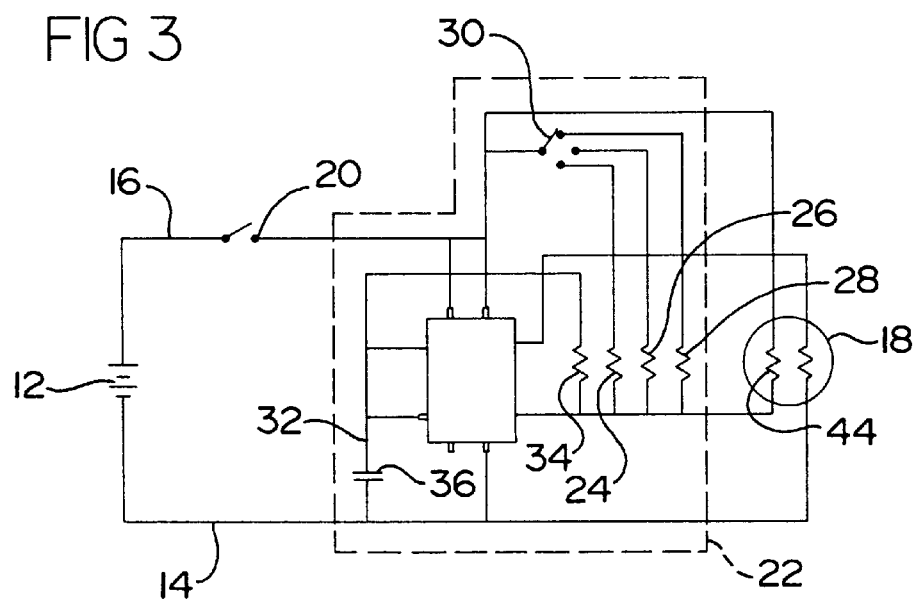
FIG. 3 is an schematic view of the electronic circuitry used with the therapeutic device hereof.
Figure 4:
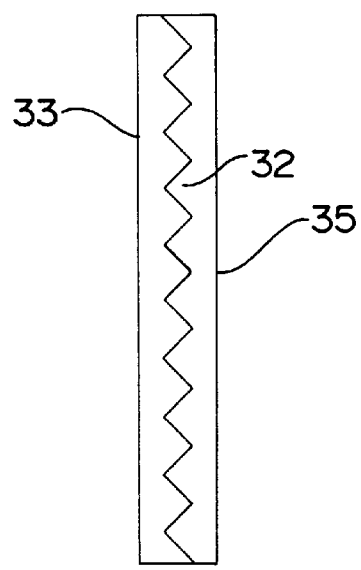
FIG. 4 is a cross-sectional view taken along line 4—4 of FIG. 1.

Now, and with reference to the drawing and, in particular, FIG. 1, there is depicted therein a therapeutic device in accordance herewith. More specifically, and as contemplated hereby, the device hereof, generally, denoted at 10, includes a source of power, such as a battery 12 or the like. The battery 12 may be any typical and commercially available nine volt battery or, alternatively, the source of power may be from a wall socket or the like providing 110 volts of AC power which is, then, converted to a D.C. source such as by a transformer incorporated into the device 10. Of course, other voltages may be used depending on the circuitry. Therefore, the source of power and the voltage is not critical hereto only the fact that it does provide a source of electrical energy of proper current and voltage. However, for purposes of describing the present invention the source shall be defined in terms of the battery 12. A pair of lead wires 14, 16 extend from the battery 12. The lead wires 14, 16 define the means for conducting electrical energy to a resistive heat generating element, generally, noted at 18. The resistive element 18, as contemplated for use in the present invention, comprises a flexible circuit board. Flexible circuit boards are well-known and commercially available devices which include conductive elements, such as copper wire or the like, is sandwiched between flexible material, such as, silicone, polycarbonate, polyethylene, polypropylene, and the like.

In a particular embodiment hereof, a switch 20 is interposed the source of power 12 and the lead wires 14, 16. The switch 20 turns the current from the source on and off.

The resistive element 18 is in electrical communication with a pulse width modulator 22 and receives current delivered therefrom. The pulse-width modulator 22 may be incorporated directly into the sandwich or laminate defining the flexible circuit board.

A pulse width modulator is an electronic device which is well-known and commercially available and which has a variable "duty cycle" output which is in essence a plurality of on-off states of output.

When connected to a resistive element the duration of the duty cycle dictates the degree of heat generated by the resistive element, as discussed below.

As shown in FIG. 3, the variation in the duty cycle is accorded by resistors 24, 26 and 28. A switch 30 is selectively movable between the resistors 24, 26 and 28 to alter or set the duty cycle. An R-C circuit 32 defined by a resistor 34 and a capacitor 36 sets the frequency. The interrelationship between the R-C circuit and the resistors 24, 26 and 28 is known to the skilled artisan.

By defining the resistive element as a flexible circuit board there is provided even distribution of heat throughout the resistive element as well as imparting flexibility to enable the device to conform to the curvature of the user's skin. As noted hereinabove, typically, such resistive elements are fabricated by interposing a circuit 32 between sheets or layers of flexible, non-conductive synthetic resinous layers 33 and 35, formed from suitable materials, such as KAPTON or the like. The circuit boards generate heat upon the application of electrical current therethrough. Flexible circuit boards of the type contemplated for use herein are well known and commercially available, such as that sold by Minco, Inc.

It is to be appreciated that the device hereof, upon the application of electricity across the circuit board creates or generates heat due to the resistance of the conductor. Because of the flexibility of the resistive element it can be emplaced for topical application in localized areas which can conform to the curvature of the skin of the user.

In a particularly preferred embodiment hereof, and as shown in FIG. 2, it is contemplated that the therapeutic device 10 hereof be used in conjunction with a dermal bandage 38. Such dermal bandages 38 are well known and commercially available and generally comprises an adhesive strip 40 and a medially disposed gauze padding 42 which is affixed to the adhesive strip 36 by any suitable means, such as by sonic welding, an adhesive or the like. The gauze padding 42 is, usually, a multi-layered padding created by placing sheets of gauze in overlying relationship. The padding 42 is, typically, used to absorb body fluids which seep from openings, such as cuts, abrasions and the like.

In accordance herewith the resistive element 18 is inserted into the gauze padding 42 of the bandage 38 behind the outermost layer. Preferably, the resistive element is disposed intermediate the adhesive strip 40 and the first layer of gauze. By emplacing the therapeutic device 10 within the gauze padding 42 an insulative barrier is created to protect the skin from direct application of the heat, thus, precluding a burning of the skin.

Alternatively, a pocket (not shown) may be provided intermediate the gauze and the bandage in which is disposed the resistive element. The actual material of construction for the strip, per se, is selected such that heat generated by the resistive element is sufficient for therapeutic applications while not being sufficiently high as to melt the adhesive strip and/or bandage or to cause combustion of the gauze layer. Of course, the strip itself may have any desired configuration.

It has been found that the unit defined by the bandage and therapeutic device, when applied to a dermal eruption for a sufficient period of time, ranging from about 1 to about 4 hours, in repetitive episodes, will produce sufficient heat to cause the dermal eruption to cause to a head and open. The gauze co-acts with the therapeutic device to absorb the body fluids emanating upon opening the dermal eruption.

Thus, in a further aspect hereof, the present invention provides a combined bandage and heat generating therapeutic device.

Referring, again to FIG. 3, it is further contemplated in the practice of the present invention that a feedback element 44 be incorporated into the circuit. The feedback element 44 maintains power or current flowing to the resistive element 18 as the source of power, i.e. the battery, loads down. Similarly, the feedback element, which is a resistor, sets the desired temperature generated by the device. In essence, the feedback functions as a thermostat having a selected temperature in relation to the selected resistor 24, 26 or 28.

Preferably, the feedback is incorporated as part of the circuit board itself which comprises the resistive element 18.

As the power wanes from the battery, the feedback provides sufficient compensation to the pulse width modulator to maintain the heat generated by the element 18 for some period of time, until the battery 12 can be replaced.

The feedback, also, acts to prevent the potential of skin burning, since as the temperature increases the feedback element causes the pulse width modulator to decrease the duty cycle, thus, stabilizing the temperature.

It is to be appreciated from the preceding that the present invention provides a therapeutic device for applying localized heat which, in combination with a bandage, not only maintains the device in place but, also, provides an insulative barrier to prevent the potential of burning of the skin. Furthermore, the present invention includes means for regulating the degree of heat to be applied to the localized area as well as incorporating means for maintaining the heat even as the source of power ages or its power wanes. Further, the feedback or pulse width modulator can be combined into a single circuit board which is, then, laminated to the flexible sheets and which has the lead wires 14, 16 extending thereto (FIG. 2). Preferably, the pulse width modulator is maintained separate and apart from the feedback element, which itself, is incorporated into the resistive element.

While the present device has particular dermatological application, other uses are within the scope hereof. Having thus described the invention what is claimed is:

1. A therapeutic device which comprises:
    (a) a dermal bandage having an adhesive strip and a medially disposed gauze pad secured to the adhesive strip, the adhesive strip extending beyond the periphery of the medially disposed gauze pad, and;
    (b) a heat generating source comprising:
        (1) a source of electrical energy,
        (2) means of conducting electrical energy from the source and
        (3) a resistive element comprising a flexible circuit board in electrical communication with the means for conducing, the resistive element being disposed within the gauze pad.

2. The device of claim 1 which further comprises a pulse width modulator interposed the source of electrical energy and the flexible circuit board.

3. The device of claim 2 wherein the pulse width modulator has a variable duty cycle.

* * * * *